(12) United States Patent
Hillisch et al.

(10) Patent No.: US 7,419,972 B2
(45) Date of Patent: Sep. 2, 2008

(54) 2-SUBSTITUTED ESTRA-1,3,5(10)-TRIEN-17-ONES AS INHIBITORS OF 17β-HYDROXY STEROID DEHYDROGENASE TYPE 1

(75) Inventors: Alexander Hillisch, Velbert (DE); Olaf Peters, Tabarz (DE); Christian Gege, Ehingen (DE); Wilko Regenhardt, Munich (DE); Andrea Rosinus, Munich (DE); Jerzy Adamski, Munich (DE); Gabriele Moeller, Munich (DE); Walter Elger, Berlin (DE); Birgitt Schneider, Jena (DE); Ulrich Bothe, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 11/154,947

(22) Filed: Jun. 17, 2005

(65) Prior Publication Data

US 2006/0009434 A1 Jan. 12, 2006

Related U.S. Application Data

(60) Provisional application No. 60/584,480, filed on Jul. 2, 2004.

(30) Foreign Application Priority Data

Jul. 2, 2004 (DE) .................. 10 2004 032 674

(51) Int. Cl.
*A61K 31/56* (2006.01)
*A61K 31/16* (2006.01)
*C07J 1/00* (2006.01)
*C07J 31/00* (2006.01)

(52) U.S. Cl. .................. 514/178; 514/182; 514/614; 514/625; 514/626; 552/525; 552/536

(58) Field of Classification Search .................. 552/525, 552/536; 514/178, 182, 614, 625, 626
See application file for complete search history.

(56) References Cited

U.S. PATENT DOCUMENTS

| | | | | |
|---|---|---|---|---|
| 3,562,260 | A | * | 2/1971 | De Ruggieri et al. ......... 540/117 |
| 6,127,401 | A | * | 10/2000 | Singh et al. .................. 514/410 |
| 6,747,018 | B2 | * | 6/2004 | Tanabe et al. ............... 514/169 |
| 6,933,386 | B2 | * | 8/2005 | Bhide et al. .................. 544/183 |
| 2003/0073674 | A1 | | 4/2003 | Slaga et al. |
| 2004/0009959 | A1 | | 1/2004 | Potter et al. |

FOREIGN PATENT DOCUMENTS

| | | | |
|---|---|---|---|
| GB | 857 081 A | | 12/1960 |
| WO | WO 99/46279 A | | 9/1999 |
| WO | WO 00/07576 A | | 2/2000 |
| WO | WO 01/70093 A | | 9/2001 |
| WO | WO 02/15910 | * | 2/2002 |
| WO | WO 02/15910 A | | 2/2002 |
| WO | WO 02/15910 A1 | * | 2/2002 |
| WO | WO 02/32409 A | | 4/2002 |
| WO | WO 02/36605 A | | 5/2002 |
| WO | WO 02/36605 A2 | * | 5/2002 |
| WO | WO 02/062347 A | | 8/2002 |
| WO | WO 02/100877 | * | 12/2002 |
| WO | WO 2004/101595 A | | 11/2004 |
| WO | WO 2004/101595 A1 | | 11/2004 |
| WO | WO 2005/089256 A | | 9/2005 |

OTHER PUBLICATIONS

Page et al., "Efficient regioselective A-ring functionalization of oestrogens.", Tetrahedron, vol. 46(6), pp. 2059-2068, 1990.*
Kaneko et al., "The synthesis of 2- and 4-alkoxymethylestrogens", Chem. Pharm. Bull., vol. 12(2), pp. 196-203, 1964.*
Seimbille et al., "Synthesis of 2,16alpha- and 4,16alpha-difluoroestradiols and their 11beta-methoxy derivatives as potential estrogen receptor-binding radiopharmaceuticals". J. Chem. Soc., Perkin Trans. 1, pp. 657-663, 2002.*
Berg et al., "Synthesis of immunogenic C-6 derivatives of 2-methoxyestrone and 2-methoxy-17beta-estradiol and characterization of the corresponding antiserums". Hoppe-Seyler's Zeitschrift fuer Physiologische Chemie, vol. 363(7), 1982, Abstract only.*
Yoshizawa et al., "Clinical analysis on steroids. XVIII. Preparation of 6,17-dioxo-catechol estrogen and its related compounds." Yakugaku Zasshi, vol. 101(3), 1981, Abstract only.*
Database CA 'Online! Chemical Abstracts Service, Columbus, Ohio, US; Patton, Tad et al: "Estrogens V. The Relation of Estrogenic Activity and Molecular Structure" XP002353442 & Archives of Biochemistry and Biophysics, 101, 181-5 Coden: ABB1A4; ISSN: 0003-9861, 1963.

(Continued)

*Primary Examiner*—Barbara P Badio
(74) *Attorney, Agent, or Firm*—Millen, White, Zelano & Branigan, P.C.

(57) ABSTRACT

The invention relates to new 2-substituted estra-1,3,5(10)-trien-17-ones of formula I

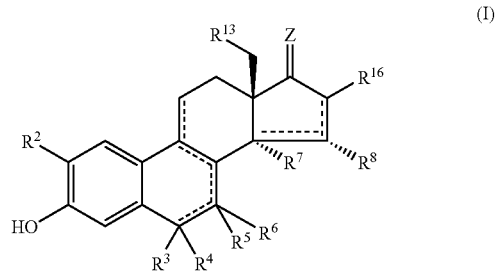

(I)

as well as their pharmaceutically acceptable salts, their methods of manufacture and use as medicaments for prophylaxis and/or therapy of estrogen-dependent diseases that can be influenced by the inhibition of 17β-hydroxy steroid dehydrogenase type 1.

26 Claims, No Drawings

OTHER PUBLICATIONS

Database CA 'Online! Chemical Abstracts Service, Columbus, Ohio, US; Jefferson, A. et al: "Abnormal Claisen Rearrangement of 3,3-Dimethylallyl Estrone Ether" XP002353443, Database Accession No. 1969:68602 & Journal of the Chemical Society Sectioni C: Organic, (2), 243-5 Coden: JS00AX; ISSN: 0022-4952, 1969.

Cushman, Mark et al: "The Effect of Exchanging Various Substituents at the 2-Position of 2-Methoxyestradiol on Cytotoxicity in Human Cancer Cell Cultures and Inhibition of Tubulin Polymerization", Journal of Medicinal Chemistry, Bd. 45, Nr. 21, Oct. 10, 2002, pp. 4748-4754, XP002368004; ISSN: 0022-2623.

Omar A-Mohsen M et al: "Synthesis, Estrogen Receptor Binding Affinity and Biological Evaluation of Some 2-Substituted Estrone Derivates" Farmaco (Rome) Bd. 52, Nr. 4, 1997, pp. 219-225; XP002368005; ISSN: 0014-827X.

Database CA 'Online! Chemical Abstracts Service, Columbus, Ohio, US; Kaneko Hidehiko et al: "Synthesis of 2-and 4-alkoxymethylestrogens" XP002368010; Database Acession No. 1964:91085 & Chemical & Pharmaceutical Bulletin 12(2), 196-203 Coden: CPBTAL; ISSN: 0009-2363, 1964.

Database CA'Online! Chemical Abstracts Service, Columbus Ohio, US; Yan Jiaming et al: "Mass Spectrometric Study on Estrogen Derivatives" XP002368011; Database Accession No. 1994:192069 & Sichuan Daxue Xuebao, Ziran Kexueban, 30(1) 88-97 Coden: Scthao; ISSN: 0490-6756, 1993.

Wood et al: "Inhibition of Superoxide Dismutase by 2-Methoxyoestradiol Analogues and Oestrogen Derivatives: Structure-Activity Relationships" Anti-Cancer Drug Design, Baskingstoke, GB, Bd. 16, Nr. 4/5, 2001 pp. 209-215; XP008055013; ISSN; 0266-9536.

Y. Seimbille et al: "Synthesis of 2,16.-Alpha.-and 4.16.Alpha.-Dilfuoroestradiols and Their 11.Beta.-Methoxy Derivatives as Potential Estrogen Receptor Binidng Radiopharmaceuticals" Journal of the Chemical Society, Perkin Transactions 1., 2002, pp. 657-663; XP002368006.

Ali et al: "Synthesis of A-Ring Fluorinated Derivatives of (17. Alpha,20E/Z)-125I! Iodovinylestradiols: Effect on Receptor Binding and Receptor-Mediated Target Tissue Uptake" Journal of Medicinal Chemistry, 36(21), 3061-72 Coden: JMCMAR; ISSN: 0022-2623, 1993, XP002368007.

Page et al: "Efficient Regioselective A-Ring Functionalization of Oestrogens" Tetrahedron, Elsevier Science Publishers, Amsterdam, NL, Bd 46, Nr. 6, 1990, pp. 2059-2068, XP000867284; ISSN: 0040-4020.

Zhang Bolton: "Synthesis of the Equine Estrogen Metabolites 2-Hydroxyequilin and 2-Hydroxyequilenin" Chemical Research in Toxicology, American Chemical Society, Washington, DC, US, Bd. 12, Nr. 2, Jan. 1999, pp. 200-203, XP002955800; ISSN: 0893-228X.

Hasrat Ali et al: "Synthesis and Receptor Binding Affinity of 7 Alpha-and 17 Alpha-Substituted 2-and 4-Chloroestradiol Derivatives" Journal of the Chemical Society, Perkin Transactions 1, Chemical Society, Letchworth, GB, Nr. 10, 1991, pp. 2485-2491, XP009043140; ISSN: 0300-922X.

Numazawa et al: "Structure-Activity Relationships of 2-, 4-, or 6-Substituted Estrogens as Aromatase Inhibitors" Journal of Steroid Biochemistry and Molcular Biology, Elsevier Science Ltd., Oxford, GB, Bd. 96, Nr. 1 Jun. 2005, pp. 51-58, XP005003329; ISSN: 0960-0760.

* cited by examiner

2-SUBSTITUTED ESTRA-1,3,5(10)-TRIEN-17-ONES AS INHIBITORS OF 17β-HYDROXY STEROID DEHYDROGENASE TYPE 1

This application claims the benefit of the filing date of U.S. Provisional Application Ser. No. 60/584,480 filed Jul. 2, 2004.

This invention relates to new 2-substituted estra-1,3,5(10)-trien-17-ones, their manufacture and use as medicaments for the treatment of estrogen-dependent diseases that can be influenced by inhibition of the 17β-hydroxy steroid dehydrogenase type 1, as well as pharmaceutical compositions that contain these compounds.

Sex hormones control the proliferation and function of steroid-sensitive normal tissue as well as malignant tissue [E. E. Baulieu, Hormones, A Complex Communication Network. In *Hormones*, eds. E. E. Baulieu and P. A. Kelly, Herman Publisher Paris and Chapman and Hall New York, 1990, pp. 147-149; D. D. Thomas, *Cancer* 53 (1984) 595-601].

Estradiol is the most active female sex hormone, which, in addition to the known effects on the reproductive system, exerts additional functions in bone and lipid metabolism and in the cardiovascular system, as well as regulatory effects in the central nervous system. It is produced primarily in the ovaries in premenopausal women. An additional large portion of the active estrogens is formed in the peripheral tissue from inactive steroid precursors, which are released into the blood in large amounts in the adrenal glands in humans.

After menopause, the estradiol level in the blood drops to about 1/10 of the content of premenopausal women [T. Thorsten, M. Tangen, K. F. Stoa, Eur. J. Cancer Clin. Oncol. 18 (1982) 333-337; A. A. van Landeghem et al., Cancer Res. 45 (1985) 2900-2906]. Starting from this time, estrogens are mainly available in the peripheral tissue via biosynthesis [F. Labrie, Intracrinology. Mol. Cell. Endocrinol. 78(1991) C113-C118].

Estrogens are taken up via the blood from tumor tissue and stimulate growth thereof.

The concentration of the intratumoral estradiol remains unchanged at a high level, however, even after menopause, comparable to that in premenopausal women [A. A. van Landeghem et al., Cancer Res. 45 (1985) 2900-2906]. The high estradiol concentration in the tumor tissue in postmenopausal women is produced by biosynthesis of estrogens in the tumor tissue.

Estradiol (E2) is formed in breast cancer tissue either via the aromatase method or the sulfatase method [Y. J. Abul-Hajj, R. Iverson, D. T. Kiang, Steroids 33 (1979) 205-222; A. Lipton et al., Cancer 59 (1987), 779-782; E. Perel et al., J. Steroid Biochem. 29 (1988) 393-399]. Androstenedione is taken up from the blood by tumor tissue, aromatized to estrone (E1) and then reduced to estradiol (E2) (aromatase method). In the sulfatase method, estrogen sulfate is converted by the steroid sulfatase into E1 and in turn reduced to E2.

The decisive last step of the steroid synthesis is catalyzed by 17β-hydroxy steroid dehydrogenases (17β-HSD), corresponding to the family of 17β-hydroxy steroid dehydrogenases/17-keto steroid reductases. These enzymes convert less active 17-keto steroids into their active 17β-hydroxy steroids and vice versa. Both estrogens and androgens show the highest affinity for the corresponding receptors in the 17β-hydroxy form, i.e., the 17β-HSD-enzymes control the biological activity of the sex hormones [H. Peltoketo et al., J. Mol. Endocrinol. 23 (1999), 1-11; P. Vihko et al., Mol. Cell. Endocrinol. 171 (2001) 71-76].

Certain extragonadal tissues such as breast and prostate tissue express reductive 17-HSDs and thus convert the precursors that circulate in the blood with low activity in the target tissues into more active forms [F. Labrie et al., Steroids 62 (1997) 148-158; H. Peltoketo et al., Horm. 55 (1999) 353-398].

Up until now, 11 different 17β-HSDs have been known. They differ in their tissue distribution, the catalytic activity, their substrate specificity, subcellular localization and by the regulation mechanism. For a large number of hydroxy steroid dehydrogenases, it was possible to show their participation in the pathogenesis of diseases of humans, for example for pseudohermaphroditism [17β-HSD 3, W. M. Geissler et al., Nat. Genet. 7 (1994) 34-39], bifunctional enzyme deficit [17β-HSD 4, E. G. van Grunsven et al., Proc. Natl. Acad. Sci. USA 95 (1998) 2128-2133], polycystic nephropathy [17β-HSD 8, M. M. Maxwell et al., J. Biol. Chem. 270 (1995) 25213-25219] and Alzheimer's disease [17β-HSD 10, S. D. Yan et al., Nature 389 (1997) 689-695; X. Y. He et al., J. Biol. Chem. 274 (1999) 15014-15019].

The human placental 17β-hydroxy steroid dehydrogenases type 1 and type 2 belong to the same steroid dehydrogenase-reductase-protein family (SDR). They are distinguished from one another by, i.a., the direction of reaction, which is catalyzed by the enzymes.

17β-HSD 1 primarily controls the reduction of estrone to estradiol [T. Puranen et al., Endocrinology 138 (1997) 3532-3539] with participation by NADPH as a co-factor [J. Z. Jin, S. X. Lin, Biochem. Biophys. Res. Commun. 259 (1999) 489-493].

In cultivated cells, the HSD 1 partially supports the reduction of androstenedione and androstanedione. It could clearly be shown, however, that phenolic substrates are preferred [M. Poutanen et al., Endocrinology 133 (1993) 2639-2644].

In comparison to 17β-HSD 1, however, the 17β-HSD 2 catalyzes the opposite reaction, namely the conversion of estradiol to estrone and of androstenedione and dihydrotestosterone to androstanedione [L. Wu et al., J. Biol. Chem. 268 (1993) 12964-12969] and preferably acts in the presence of the non-phosphorylated form of the co-factor NAD [F. Labrie et al., Steroids 62 (1997) 148-158].

17β-HSD 1 and 2 are expressed in normal mammary gland tissue [G. Söderqvist, J. Clin. Endocrinol. Metab. 83 (1998) 1190-1193; M. Miettinen, Breast Cancer Res. Treat. 57 (1999) 175-182].

In contrast to the normal breast tissue, the reductive activity (by 17β-HSD 1) in malignant breast epithelial cells is found to be increased compared to the oxidative activity (by 17β-HSD 2) [M. M. Miettinen et al., Biochem. J. 314 (1996) 839-845; V. Speirs, J. Steroid Biochem. Mol. Biol. 67 (1998) 267-274]. It was observed that estradiol is accumulated in malignant breast cells, which also points to an activity of 17β-HSD 1 [A. Vermeulen et al., Eur. J. Cancer Clin. Oncol. 22 (1986) 515-525]. In addition, it was found that in the presence of 17β-HSD 1, the administration of estrone leads in the same way to a growth of breast cancer cells just like the administration of estradiol by itself. In contrast to this, the administration of estrone by itself without 17β-HSD 1 does not produce this effect [M. M. Miettinen et al., Int. J. Cancer 68 (1996) 600-604].

The dominance of 17β-HSD 1 in malignant tissue results in increased estrogen-dependent growth and progress of tumors, while the oxidative 17β-HSD 2 protect normal breast tissue cells from an excessive estradiol effect [P. Vihko et al. Mol. Cell. Endocrinol. 171 (2000) 71-76].

In the case of endometriosis, the equilibrium between 17β-HSD 1 and 2 plays a role. 17β-HSD 1 is expressed in eutopic tissue, but the hormone-inactivating enzyme 17β-HSD 2 is completely lacking [S. E. Bulun et al. J. Mol. Endocrinol. 25 (2000) 35-42.

Also, in the case of prostate cancers, 17β-HSD 2 is reduced [J. P. Elo et al., Endocrinol. Metab. 88 (2003) 705-712].

Among the previously developed 17β-HSD 1 inhibitors, the irreversible inhibitors are distinguished from the reversible inhibitors. The irreversible inhibitors contain a reactive functional group, which inactivates the latter by forming a covalent bond with an amino acid radical of the enzyme. Known representatives of the above-mentioned group are 16-methylene-estradiols, acetylene-substituted 16-seco-estradiol [R. J. Auchus, D. F. Covey, Biochemistry 25 (1983) 7295-7300; J. L. Thomas et al., J. Biol. Chem. 258 (1983) 11500-11504; B. Tobias et al., J. Biol. Chem. 257 (1982) 2783-2786] or else 16α-haloalkyl-estradiols [K. M. Sam et al., Drug Des. Discov. 15 (1997) 157-180; M. R. Tremblay, D. Poirier, J. Steroid Biochem. Mol. Biol. 66 (1998) 179-191].

The reversible inhibitors include 16,17-pyrazole- or 16,17-isoxazole-estrone derivatives [F. Sweet et al. Biochem. Biophys. Res. Commun. 180 (1991), 1057-1063], estradiol derivatives with a long 7α-undecanamide side chain [C. Labrie et al. *Cancer Res.* 52 (1992), 610-615; S. J. Santner, R. J. Santen, J. Steroid Biochem. Mol. Biol. 45 (1993) 383-390] or with a 6β-thiaheptanamide side chain [D. Poirier, P. Dionne, S. Auger, J. Steroid Biochem. Mol. Biol. 64 (1998), 83-90].

A special case as a 17β-HSD 1-inhibitor is the 16-oxoestrone: at a neutral pH of 7.2, it includes the reversible inhibitors, and under basic conditions at a pH of 8.5, it includes the irreversible inhibitors [H. Inano, B. Tamaoki, Eur. J. Biochem. 129 (1983) 691-695].

The previously known, both reversible and irreversible inhibitors have only one moderate activity as 17β-HSD 1 inhibitors.

The first hybrid inhibitor was recently found by modeling studies [M. Tremblay, D. Poirier et al., FASEB 13 (2002) 1829-1831]. The hybrid inhibitor, in which estradiol is linked to adenosine via a spacer that consists of 8 methylene groups at 16-position, inhibits the 17β-HSD 1 as the best inhibitor to date with an $IC_{50}$ value of 52 nmol.

Because of the size of this molecule, making this compound bioavailable orally would be difficult. It is not unlikely that the molecule undergoes a cross reaction with other NAD (P)(H)-dependent enzymes.

From the known prior art, 17β-HSD 1 is a target for local inhibition of the estradiol biosynthesis. Accompanying treatment with antihormones, which are to prevent the binding of the active steroid to the corresponding receptor, 17β-HSD 1 inhibitors can be used to support treatment of estrogen-dependent diseases.

The object of this invention is therefore to provide additional compounds that inhibit the 17β-HSD 1 selectively. These compounds are to be suitable for treating estrogen-dependent diseases as well as hormone-dependent tumor diseases, which can be influenced by inhibition of the 17β-hydroxy steroid dehydrogenase type 1.

Additional subjects of this invention are the manufacture and use of these compounds as medicaments for the treatment of estrogen-dependent diseases as well as hormone-dependent tumor diseases, which can be influenced by inhibition of 17β-hydroxy steroid dehydrogenase type 1.

The object is achieved according to this invention by the provision of new 2-substituted estra-1,3,5(10)-trien-17-ones of general formula I

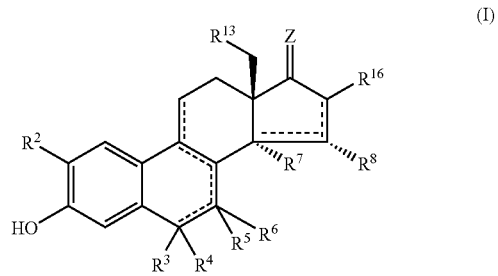

in which
  $R^2$ means a saturated or unsaturated $C_1$-$C_8$-alkyl group, a $C_1$-$C_5$-alkyloxy group, an aralkyl radical or alkylaryl radical, a radical —O—$C_nF_mH_o$, whereby n=1, 2, 3, 4, 5 or 6, m≧1 and m+o=2n+1, or a group $CH_2XY$, in which X stands for an oxygen atom and Y stands for an alkyl radical with 1 to 4 carbon atoms, as well as a halogen atom or a nitrile group,
  $R^{13}$ means a hydrogen atom or a methyl group,
  $R^{16}$ means a hydrogen atom or a fluorine atom,
  Z means an oxygen atom or a sulfur atom,
  $R^3$ and $R^5$, in each case independently of one another, mean an α- or β-position hydrogen atom,
  $R^4$ and $R^6$, in each case independently of one another, mean an α- or β-position hydrogen atom, a $C_1$-$C_5$-alkyl group, a $C_1$-$C_5$-alkyloxy group, a $C_1$-$C_5$-acyl group or a hydroxy group or an aralkyl radical or alkylaryl radical,
  $R_3$ and $R_4$ together mean an oxygen atom,
  $R_5$ and $R_6$ together mean an oxygen atom,
  $R^7$ and $R^8$ in each case mean a hydrogen atom or together a $CH_2$ group, whereby the dotted lines in the B-, C- and D-ring of the steroid skeleton additionally can be up to two double bonds, as well as their pharmaceutically acceptable salts.

In addition, this invention comprises the new compounds as pharmaceutical active ingredients, their production, their therapeutic application and pharmaceutical dispensing forms that contain the new substances.

The compounds of general formula (I) according to the invention or their pharmaceutically acceptable salts can be used for the production of a pharmaceutical agent, in particular for treating estrogen-dependent diseases as well as hormone-dependent tumor diseases that can be influenced by inhibition of the 17β-hydroxy steroid dehydrogenase type 1.

It was determined that the low-molecular 2-substituted estra-1,3,5(10)-trien-17-ones according to the invention produce a selective inhibition of the 17β-HSD 1-enzyme activity in vitro that is stronger than the previously known 17β-HSD 1 inhibitors.

Unless further specified otherwise, for the purposes of this invention this is an aryl radical that optionally can be substituted by a phenyl, 1- or 2-naphthyl radical, whereby the phenyl radical is preferred. Unless expressly indicated otherwise, aryl also always includes a heteroaryl radical. Examples of a heteroaryl radical are the 2-, 3-, or 4-pyridinyl radical, the 2- or 3-furyl radical, the 2- or 3-thienyl radical, the 2- or 3-pyrrolyl radical, the 2-, 4- or 5-imidazolyl radical, the pyrazinyl radical, the 2, 4 or 5-pyrimidinyl radical or the 3- or 4-pyridazinyl radical.

As substituents for an aryl or heteroaryl radical, for example, a methyl, ethyl, trifluoromethyl, pentafluoroethyl, trifluoromethylthio, methoxy, ethoxy, nitro, cyano, halogen (fluorine, chlorine, bromine, iodine), hydroxy, amino, mono ($C_{1-8}$-alkyl) or di($C_{1-8}$-alkyl)amino, whereby both alkyl groups are identical or different, di(aralkyl)amino, whereby both aralkyl groups are identical or different, can be mentioned.

The $C_1$-$C_8$-alkyl groups for $R^2$ can be saturated or unsaturated and can be partially or completely substituted. As representatives of the saturated alkyl radicals, a methyl, ethyl, n-propyl-, iso-propyl-, n-, iso-, or tert.-butyl, n-, iso- or neo-pentyl group or else n-hexyl as well as n-heptyl can be mentioned. Methyl, ethyl and propyl are preferred.

Allyl, vinyl and ethinyl stand as representatives for unsaturated alkyl radicals.

For the partially or completely fluorinated alkyl radical in substituent $R^3$, for example, a trifluoromethyl, pentafluoroethyl or 2,2,2-trifluoroethyl radical is suitable.

A methoxy, ethoxy, n-propoxy, iso-propoxy, n-, iso-, or tert.-butoxy, n-, iso- or neo-pentoxy group can stand for the $C_1$-$C_5$-alkoxy radical $R^2$.

In the case of $R^2$, a chlorine, iodine or bromine atom can stand for a halogen.

A $C_1$-$C_5$-acyl radical is defined as a formyl, acetyl, propionyl, butyryl or pentanoyl radical.

Preferred according to this invention are compounds of general formula I, in which $R^2$ is a $C_1$-$C_5$-alkoxy, $C_1$-$C_5$-alkyl or $C_2$-$C_3$-alkenyl or $C_2$-$C_3$-alkinyl or bromine, iodine or chlorine, or a nitrile radical, and $R^{13}$ is a hydrogen atom.

The compounds that are mentioned below and use thereof are preferred according to the invention:
1) 2-Chloro-3-hydroxy-18a-homoestra-1,3,5(10)-trien-17-one 1
2) 3-Hydroxy-2-pentanoyl-estra-1,3,5(10)-trien-17-one 2
3) 2-Chloro-16α-fluoro-3-hydroxy-estra-1,3,5(10)-trien-17-one 3
4) 2-Chloro-16β-fluoro-3-hydroxy-estra-1,3,5(10)-trien-17-one 4
5) 3-Hydroxy-2-methoxy-14α,15α-cyclopropa[a]estra-1,3,5(10),8-tetraen-17-one 5
6) 3-Hydroxy-2-methoxy-estra-1,3,5(10)-triene-17-thione 6
7) 3-Hydroxy-2-methoxymethyl-estra-1,3,5(10)-trien-17-one 7
8) 3-Hydroxy-2-methyl-estra-1,3,5(10)-trien-17-one 8
9) 2-Ethyl-3-hydroxy-estra-1,3,5(10)-trien-17-one 23
10) 3-Hydroxy-2-propyl-estra-1,3,5(10)-trien-17-one 9
11)₃-Hydroxy-2-(prop-2'-enyl)-estra-1,3,5(10)-trien-17-one 10
12) 2-Chloro-3-hydroxy-estra-1,3,5(10)-trien-17-one 11
13) 2-Bromo-3-hydroxy-estra-1,3,5(10)-trien-17-one
14) 2-Cyano-3-hydroxy-estra-1,3,5(10)-trien-17-one 12
15) 3-Hydroxy-2-iodo-estra-1,3,5(10)-triene-7,17-dione 13
16) 3-Hydroxy-2-methoxy-estra-1,3,5(10)-triene-6,17-dione 14
17) 3,7β-Dihydroxy-2-iodo-estra-1,3,5(10)-trien-17-one 15
18) 7β-Acetoxy-3-hydroxy-2-iodo-estra-1,3,5(10)-trien-17-one 16
19) 2-Chloro-3-hydroxy-7α-methyl-estra-1,3,5(10)-trien-17-one 17
20) 3-Hydroxy-2-methoxy-estra-1,3,5(10),6-tetraen-17-one 18
21) 3-Hydroxy-2-phenylethinyl-estra-1,3,5(10)-trien-17-one 19
22) 2-Hexyl-3-hydroxy-estra-1,3,5(10)-trien-17-one 20
23) 3-Hydroxy-2-(2'-phenyl-ethyl)estra-1,3,5(10)-trien-17-one 21
24) 3-Hydroxy-2-(3'-phenyl-propyl)-estra-1,3,5(10)-trien-17-one 22
25) 3-Hydroxy-2-pentanoyl-estra-1,3,5(10)-trien-17-one
26) 2-Bromo-3-hydroxy-estra-1,3,5(10)-triene-6,17-dione
27) 2-Chloro-3-hydroxy-estra-1,3,5(10)-triene-6,17-dione
28) 2-Bromo-3-hydroxy-estra-1,3,5(10)-triene-7,17-dione
29) 2-Chloro-3-hydroxy-estra-1,3,5(10)-triene-7,17-dione
30) 2-Cyano-3-hydroxy-estra-1,3,5(10)-triene-6,17-dione
31) 2-Cyano-3-hydroxy-estra-1,3,5(10)-triene-7,17-dione
32) 2-Bromo-3-hydroxy-estra-1,3,5(10)-triene-17-thione
33) 2-Chloro-3-hydroxy-estra-1,3,5(10)-triene-17-thione
34) 2-Cyano-3-hydroxy-estra-1,3,5(10)-triene-17-thione
35) 3-Hydroxy-2-iodo-estra-1,3,5(10)-triene-17-thione
36)₃-Hydroxy-2-iodo-estra-1,3,5(10)-triene-6,17-dione 24
37) 2-Chloro-3-hydroxy-14α,15α-cyclopropa[a]estra-1,3,5(10),8-tetraen-17-one
38) 3-Hydroxy-2-iodo-14α,15α-cyclopropa[a]estra-1,3,5(10),8-tetraen-17-one
39) 2-Bromo-3-hydroxy-14α,15α-cyclopropa[a]estra-1,3,5(10),8-tetraen-17-one
40) 2-Cyano-3-hydroxy-14α,15α-cyclopropa[a]estra-1,3,5(10),8-tetraen-17-one
41) 3-Hydroxy-14α,15α-cyclopropa[a]estra-1,3,5(10),8-tetraen-17-one
42)₃-Hydroxy-2-propyl-14α,15α-cyclopropa[a]estra-1,3,5(10),8-tetraen-17-one
43) 7β-Acetoxy-2-chloro-3-hydroxy-estra-1,3,5(10)-trien-17-one
44) 7 β-Acetoxy-2-cyano-3-hydroxy-estra-1,3,5(10)-trien-17-one
45) 7β-Acetoxy-2-bromo-3-hydroxy-estra-1,3,5(10)-trien-17-one
46) 3-Hydroxy-2-methyl-estra-1,3,5(10)-triene-6,17-dione
47) 3-Hydroxy-2-propyl-estra-1,3,5(10)-triene-6,17-dione
48) 3-Hydroxy-2-(prop-2'-enyl)-estra-1,3,5(10)-triene-6,17-dione
49) 3-Hydroxy-2-methyl-estra-1,3,5(10)-triene-7,17-dione
50) 3-Hydroxy-2-propyl-estra-1,3,5(10)-triene-7,17-dione
51) 3-Hydroxy-2-(prop-2'-enyl)-estra-1,3,5(10)-triene-7,17-dione
52) 7β-Acetoxy-3-hydroxy-2-methyl-estra-1,3,5(10)-trien-17-one
53) 7β-Acetoxy-3-hydroxy-2-propyl-estra-1,3,5(10)-trien-17-one
54) 7β-Acetoxy-3-hydroxy-2-(prop-2'-enyl)-estra-1,3,5(10)-trien-17-one
55) 2-Bromo-3-hydroxy-18a-homoestra-1,3,5(10)-trien-17-one
56) 3-Hydroxy-2-iodo-18a-homoestra-1,3,5(10)-trien-17-one
57) 2-Cyano-3-hydroxy-18a-homoestra-1,3,5(10)-trien-17-one
58) 2-Bromo-3-hydroxy-7α-methyl-estra-1,3,5(10)-trien-17-one
59) 2-Cyano-3-hydroxy-7α-methyl-estra-1,3,5(10)-trien-17-one
60) 3-Hydroxy-2-iodo-7α-methyl-estra-1,3,5(10)-trien-17-one
61) 3-Hydroxy-2-iodo-estra-1,3,5(10)-trien-17-one
62) 3-Hydroxy-2-methoxy-estra-1,3,5(10),14-tetraen-17-one
63) 16α-Fluoro-3-hydroxy-2-(2'-phenyl-ethyl)-estra-1,3,5(10)-trien-17-one
64) 16β-Fluoro-3-hydroxy-2-(2'-phenyl-ethyl)-estra-1,3,5(10)-trien-17-one
65) 3-Hydroxy-2-(2'-phenyl-ethyl)-18a-homoestra-1,3,5(10)-trien-17-one
66) 16α-Fluoro-3-hydroxy-2-(2'-phenyl-ethyl)-18a-homoestra-1,3,5(10)-trien-17-one 67) 16β-Fluoro-3-hydroxy-2-(2'-phenyl-ethyl)-18a-homoestra-1,3,5(10)-trien-17-one
68) 16α-Fluoro-3-hydroxy-2-phenylethinyl-estra-1,3,5(10)-trien-17-one
69) 16β-Fluoro-3-hydroxy-2-phenylethinyl-estra-1,3,5(10)-trien-17-one
70) 2-Chloro-16α-fluoro-3-hydroxy-18a-homoestra-1,3,5(10)-trien-17-one
71) 2-Chloro-16β-fluoro-3-hydroxy-18a-homoestra-1,3,5(10)-trien-17-one
72) 2-Cyano-16α-fluoro-3-hydroxy-estra-1,3,5(10)-trien-17-one
73) 2-Cyano-16β-fluoro-3-hydroxy-estra-1,3,5(10)-trien-17-one
74) 2-Cyano-16α-fluoro-3-hydroxy-18a-homoestra-1,3,5(10)-trien-17-one
75) 2-Cyano-16β-fluoro-3-hydroxy-18a-homoestra-1,3,5(10)-trien-17-one
76) 2-Chloro-16α-fluoro-3-hydroxy-14α,15α-cyclopropa[a]estra-1,3,5(10),8-tetraen-17-one
77) 2-Chloro-16β-fluoro-3-hydroxy-14α,15α-cyclopropa[a]estra-1,3,5(10),8-tetraen-17-one
78) 2-Cyano-16α-fluoro-3-hydroxy-14α,15α-cyclopropa[a]estra-1,3,5(10),8-tetraen-17-one
79) 2-Cyano-16β-fluoro-3-hydroxy-14α,15α-cyclopropa[a]estra-1,3,5(10),8-tetraen-17-one
80) 3-Hydroxy-2-(2'-phenyl-ethyl)-14α,15α-cyclopropa[a]estra-1,3,5(10),8-tetraen-17-one
81) 16α-Fluoro-3-hydroxy-2-(2'-phenyl-ethyl)-14α,15α-cyclopropa[a]estra-1,3,5(10),8-tetraen-17-one
82) 16β-Fluoro-3-hydroxy-2-(2'-phenyl-ethyl)-14α,15α-cyclopropa[a]estra-1,3,5(10),8-tetraen-17-one
83) 2-Chloro-3-hydroxy-14α,15α-cyclopropa[a]estra-1,3,5(10)-trien-17-one
84) 2-Chloro-16β-fluoro-3-hydroxy-14α,15α-cyclopropa[a]estra-1,3,5(10)-trien-17-one
85) 2-Cyano-3-hydroxy-14α,15α-cyclopropa[a]estra-1,3,5(10)-trien-17-one
86) 2-Cyano-16β-fluoro-3-hydroxy-14α,15α-cyclopropa[a]estra-1,3,5(10)-trien-17-one
87) 3-Hydroxy-2-(2'-phenyl-ethyl)-14α,15α-cyclopropa[a]estra-1,3,5(10)-trien-17-one
88) 16β-Fluoro-3-hydroxy-2-(2'-phenyl-ethyl)-14α,15α-cyclopropa[a]estra-1,3,5(10)-trien-17-one, Pharmacological Data Inhibition of the Activity of Human 17β-Hydroxy Steroid Dehydrogenase Type 1

The test method is well described in the literature [Adamski, J., Sierralta, W. D., Jungblut, P. W., Acta Endocrinol (Copenh.) 121(2) (1989), 161-7] and is depicted below.

Human 17β-hydroxy steroid dehydrogenases (17β-HSDs) are over-expressed in $E.\ coli$ bacteria as His-Tag proteins or as GST-fusion proteins. The suspensions of the bacterial pellets in isotonic common salt solution are used for the determination of enzyme activities of the 17β-HSDs or for the study of their influence by potential inhibitors (estrogen derivatives).

The measurements are made in double determination and, if necessary, at various concentrations of potential inhibitors (e.g., in determining the $IC_{50}$ values). In addition to the target enzyme 17β-HSD1, other steroid-metabolizing enzymes are included in the test to study cross reactivities of estrogen derivatives.

$^3$H-Labeled substrate, bacterial suspensions, DMSO (in the control batch; final 1%) or the potential inhibitors (estrone derivatives in DMSO) as well as suitable cofactors (NADP(H) or NAD(H); 5 mg/ml in $H_2O$) are added to a defined volume of 100 mmol of sodium phosphate buffer. The incubation of the samples is carried out at 37° C. in a water bath while being shaken, such that in the control (without substances to be tested), a conversion of about 30% is achieved.

The separation of radiolabeled substrate and product is then carried out, after extraction with 1 ml of reversed phase-(RP-18)-cartridges, by means of HPLC on an RP18 column with acetonitrile:water 1:1 (v/v) as a mobile phase. The radioactivity is detected with the aid of a flow-scintillation counter.

The evaluation of the substrate conversion with and without substances to be tested is performed by the integration of the substrate and product peaks. The conversion of the control normalized to 100% conversion.

TABLE 1

Inhibition of the Human 17β-Hydroxy Steroid Dehydrogenase

| Structure | 17βHSD1 $IC_{50}$ [nmol] |
|---|---|
| 1 | 121 |
| 3 | 101 |
| 4 | 35 |
| 11 | 140 |
| 12 | 148 |
| 19 | 56 |
| 21 | 47 |
| 23 | 89 |
| Estrone | 109 |

Dosage

In general, satisfactory results in the treatment of estrogen-dependent diseases as well as hormone-dependent tumor diseases can be expected if the daily doses encompass a range of 5 µg to 50 mg of the compound according to the invention per kg of body weight. In the case of larger mammals, for example humans, a recommended daily dose lies in the range of 10 µg to 30 mg per kg of body weight.

Suitable dosages for the compounds according to the invention are from 0.005 to 50 mg per day per kg of body weight, depending on the age and constitution of the patient, whereby the necessary daily dose can be administered one or more times.

The formulation of the pharmaceutical preparations based on the new compounds is carried out in a way that is known in the art by the active ingredient being processed with the vehicles, fillers, substances that influence decomposition, binding agents, moisturizers, lubricants, absorbents, diluents, taste corrigents, coloring agents, etc., that are commonly used in galenicals, and converted into the desired form of administration. In this case, reference is made to Remington's Pharmaceutical Science, 15$^{th}$ Ed., Mack Publishing Company, East Pennsylvania (1980).

For oral administration, in particular tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local therapy.

For pulmonary administration of the new compounds, the latter can be used in the form of aerosols and inhalants.

For topical application, formulations in gels, ointments, fatty ointments, creams, pastes, powders, milk and tinctures are possible. The dosage of the compounds of general formula I should be 0.01%-20% in these preparations to achieve an adequate pharmacological action.

This invention comprises the compounds of general formula I as well as use thereof for the production of a pharmaceutical agent, in particular for treating estrogen-dependent diseases, which can be positively influenced by the inhibition of the 17β-hydroxy steroid dehydrogenase.

The compounds of general formula I according to the invention are preferably used for the production of a pharmaceutical agent for treating hormone-dependent tumor diseases of male and female reproductive glands, male and female sex organs including the mammary glands, in particular prostate cancers or breast cancers.

In addition, the compounds according to the invention for the production of a pharmaceutical agent for treating endometriosis are preferred.

This invention also relates to the pharmaceutical compositions that contain at least one compound according to the invention, optionally in the form of a pharmaceutically/pharmacologically compatible salt, without or together with pharmaceutically compatible adjuvants and/or vehicles.

These pharmaceutical compositions and pharmaceutical agents can be provided for oral, rectal, vaginal, subcutaneous, percutaneous, intravenous or intramuscular administration. In addition to commonly used vehicles and/or diluents, they contain at least one compound according to the invention.

The pharmaceutical agents of the invention are produced with commonly used solid or liquid vehicles or diluents and the commonly used pharmaceutical-technical adjuvants corresponding to the desired type of administration with a suitable dosage in a known way. The preferred preparations consist in a dispensing form that is suitable for oral administration. Such dispensing forms are, for example, tablets, film tablets, coated tablets, capsules, pills, powders, solutions or suspensions or else depot forms.

The pharmaceutical compositions that contain at least one of the compounds according to the invention are preferably administered orally.

Parenteral preparations, such as injection solutions, are also considered. In addition, for example, suppositories and agents for vaginal application can also be mentioned as preparations.

Corresponding tablets can be obtained by, for example, mixing the active ingredient with known adjuvants, for example inert diluents, such as dextrose, sugar, sorbitol, mannitol, polyvinylpyrrolidone, explosives such as corn starch or alginic acid, binding agents such as starch or gelatin, lubricants such as magnesium stearate or talc and/or agents for achieving a depot effect, such as carboxylpolymethylene, carboxyl methyl cellulose, cellulose acetate phthalate or polyvinyl acetate. The tablets can also consist of several layers.

Coated tablets can accordingly be produced by coating cores, which are produced analogously to the tablets, with agents that are commonly used in tablet coatings, for example polyvinylpyrrolidone or shellac, gum arabic, talc, titanium oxide or sugar. In this case, the coated tablet shell can also consist of several layers, whereby the adjuvants that are mentioned above with the tablets can be used.

Solutions or suspensions of the compounds of general formula I according to the invention can additionally contain taste-improving agents, such as saccharine, cyclamate, or sugar, as well as, e.g., flavoring substances such as vanilla or orange extract. In addition, they can contain suspending adjuvants, such as sodium carboxymethyl cellulose, or preservatives, such as p-hydroxybenzoates.

The compounds of general formula I that contain capsules can be produced by, for example, the compound(s) of general formula I being mixed with an inert vehicle such as lactose or sorbitol and being encapsulated in gelatine capsules.

Suitable suppositories can be produced by, for example, mixing with vehicles that are provided for this purpose, such as neutral fats or polyethylene glycol or derivatives thereof.

The compounds according to the invention can be administered for prophylaxis and for therapy of breast cancer or prostate cancer or endometriosis in combination with one or more of the following active ingredients:

1) Antiandrogens, such as cyproterone acetate, flutamide, casodex, etc.
2) Gonadotropin hormone (GnRH) agonists such as synarel, lupron, busrelin
3) Aromatase inhibitors such as anastrozole, formestane, letrozole, exemestane
4) 5α-Reductase inhibitors, such as finasteride
5) Cytostatic agents, such as vinblastine, daunorubicin
6) VEGF-kinase inhibitors
7) Antigestagens, such as onapristones, mifepristones
8) Antiestrogens such as tamoxifen
9) Antisense oligonucleotides
10) EGF Antibodies Moreover, the compounds of general formula I according to the invention can be used for therapy and prophylaxis of other pathological conditions that are not mentioned above.

The following examples are used for a more detailed explanation of the subject of the invention, without intending that it be limited to these examples.

The functionalization of the C Atom 2 of an estra-1,3,5 (10)-trien-17-one derivative is preferably carried out by Friedel-Crafts acylation as described in the literature (T. Nambara et al., Chem. Pharm. Bull. 1979, 18, 474). After alteration of the protective group in 3-position, a 2-carboxy-estra-1,3,5(10)-trien-17-one is generated by Baeyer-Villiger oxidation (M. B. Smith, J. March, *March's Advanced Organic Chemistry*, 5$^{th}$ Edition, Wiley Sons 2001, 1417-1418 and literature cited therein). The ester is saponified and converted with the corresponding alkyl halide under basic conditions into a 2-alkyl ether. The cleavage of the protective group in 3-position is carried out as described in the literature (T. W. Greene, P. G. M. Wuts, *Protective Groups in Organic Synthesis*, Wiley & Sons, 1999, 249-275).

The 2-acyl derivatives that are produced by the Friedel-Crafts acylation, however, can also be reacted by reduction with sodium borohydride and subsequent hydrogenation to 2-alkyl-estradiol derivatives and can be converted by means of Oppenauer oxidation on C-17 (C. Djerassi, *Org. React.* 1951, 6, 207) into the corresponding 2-alkyl estrone derivatives.

In compounds that contain additional double bonds in the steroid skeleton and/or a methylene bridge between C-14 and C-15, the 2-hydroxylation is carried out by ortho-metallization, whereby preferably an ether protective group (H. E. Paaren, S. R. Duff, U.S. Pat. No. 6,448,419; P. S. Kiuru, K. Wähälä, *Steroids* 2003, 68, 373) or a carbamate protective group (V. Snieckus, *Chem. Rev.* 1990, 90, 879-933) is used as an ortho-directing protective group. The electrophilic substitution is carried out after 2-lithiation with trialkyl borate and subsequent basic oxidation with hydrogen peroxide. The selectively obtained 2-hydroxy group is then converted in a known way (Z. Wang, M. Cushman, *Synth. Commun.* 1998, 28, 4431) into a 2-alkoxy compound and deprived of protection on the C-3 atom. Subsequent Oppenauer oxidation (C. Djerassi, *Org. React.* 1951, 6, 207, S. Schwarz et al. *Pharmazie* 2001, 56, 843-849) yields the 17-keto compounds.

2-Halogen compounds are produced by ortho-thallation of 3-acetyl-estrone and subsequent reaction with a copper halide (P. C. Bulman Page, F. Hussain, J. L. Maggs, P. Morgan, B. K. Park, *Tetrahedron,* 1990, 46, 2059-2068).

2-Alkinyl compounds are produced starting from 3-acetyl-2-iodo-estrone by means of a Sonogashira coupling. By partial or complete catalytic hydrogenation and subsequent deacetylation, corresponding 2-alkenyl or 2-alkyl compounds are obtained.

As an alternative, short-chain 2-alkyl or 2-alkenyl substituents can also be produced via an ortho-lithiation. Starting from estrone, for this purpose protective groups on C-3 and C-17 of the steroid skeleton must first be introduced. The 17-carbonyl group is converted with ethylene glycol and trimethyl orthoformate in the presence of catalytic amounts of p-toluenesulfonic acid into the corresponding ethylene acetal (Caserio Jr., F. F., Roberts, J. D., *J. Am. Chem. Soc.,* 80, 1958, 5837). Then, the 3-hydroxy group is protected with an ortho-directing protective group. The reaction is preferably performed under standard conditions with Hünig base and methoxy methyl chloride to form methoxy methyl ether (G. Stork, T. Takahashi, *J. Am. Chem. Soc.,* 1975, 99, 1275). The subsequent ortho-lithiation is carried out with sec-butyl lithium optionally in the presence of copper(I) iodide. The intermediate 2-metallate is reacted with alkyl or alkenyl iodides or -bromides to form corresponding 2-alkyl or 2-alkenyl derivatives. After the protective groups are removed in an acidic medium, the desired 2-alkyl- and alkenyl estrone derivatives are obtained.

For functionalization of the C-6 atom, first protective groups for the 3-hydroxy function as well as the 17-keto group must be introduced. As described above, the 17-keto group is preferably converted as ethylene acetal and the 3-hydroxy group into the corresponding methoxy methyl ether (G. Stork, T. Takahashi, *J. Am. Chem. Soc.,* 1975, 99, 1275). The subsequent oxidation of the benzylic 6-methylene group to form ketone is preferably carried out with chromium trioxide and 3,5-dimethylpyrazole (G. Weber, J. Schaumann, C: Carl, S. Schwarz, *J. Prakt. Chem.* 1989, 331, 223).

The corresponding 6-oxo derivatives can then be reacted under Wittig or Wadsworth-Homer conditions (M. B. Smith, J. March, *March's Advanced Organic Chemistry, 5th Edition,* Wiley Sons 2001, 1231ff and citations indicated therein) to form the corresponding 6-alkylidene compounds. The corresponding 6-alkyl derivatives can preferably be produced by catalytic hydrogenation.

After previous reduction of the 6-oxo group with sodium borohydride under standard conditions, 6-alkyl ether and 6-alkyl ester can be synthesized (Ohno, K., Nishiyama, H., Nagase, H., *Tetrahedron Lett.,* 1979, 4405 and Weber, H., Khorana, H. G., *J. Mol. Biol.,* 72, 1972, 219).

A starting substance for the functionalization of C atom 7 of an estra-1,3,5(10)-trien-17-one derivative is 7β-hydroxyestrone, which can be produced by microbiological 7β-hydroxylation of 19-nor-androstene-3,17-dione and subsequent aromatization (Squibb and Sons Inc., U.S. Pat. No. 3,401, 180, 1968). The corresponding 7-oxo derivative is obtained by Oppenauer oxidation. The further derivatization of the 7-position can be carried out as described analogously to the functionalization of the 6-position.

The synthesis of 14,15-dehydro derivatives or 15,16-dehydro derivatives can be performed analogously to known processes (see, e.g., P. N. Rao et al., *Steroids* 2002, 67, 1079).

16-Fluorinated estrone derivatives can be produced as described by A. C. Stalford et al. (*Steroids* 1997, 62, 750) or else S. Stavber et al. (*Synthesis* 2002, 2609).

The above-mentioned processes can be used also correspondingly to 18a-homo-estrone derivatives (P. N. Rao, J. W. Cessac, *Steroids* 2002, 67, 1065 and literature that is cited therein).

Production Process

General Synthesis Instructions A:

Single-Pot Hydrolysis of 3-Methoxy Methyl Ether as well as of the 17-Ethylene Acetal of a 3-Methoxymethoxy-estra-1,3,5(10)-trien-17-one-17-ethylene Acetal Derivative 100 mg of p-toluenesulfonic acid was added to a solution of 100 mg of a 3-methoxymethoxy-estra-1,3,5(10)-trien-17-one-17-ethylene acetal derivative in 5 ml of dichloromethane/acetone. The solution was stirred overnight, then mixed with 5 ml of a saturated sodium bicarbonate solution, and the organic phase was separated from the aqueous phase. The aqueous phase was with dichloromethane (3×5 ml). The combined organic phases were washed with a saturated NaCl solution, dried on sodium sulfate and concentrated by evaporation in a rotary evaporator. The purification was carried out by flash chromatography (cyclohexane/ethyl acetate).

General Synthesis Instructions B:

Production of 2-Alkinyl- and 2-Alkylestrone Derivatives 0.5 mmol (219 mg) of 3-acetoxy-2-iodo-estra-1,3,5(10)-triene was dissolved in 16 ml of triethylamine/THF (3:1), mixed with 10 mg of palladium(II) acetate, 8 mg of copper(I) iodide, 10 mg of triphenylphosphine and 1 mmol of an alkinyl compound, and stirred for 45 minutes at room temperature under argon. Then, it was diluted with ethyl acetate, washed with 1N hydrochloric acid, saturated sodium bicarbonate solution and saturated sodium chloride solution and dried on sodium sulfate. The solvent was then distilled off in a rotary evaporator. The purification was carried out by flash chromatography (cyclohexane/ethyl acetate).

For the production of 2-alkinyl estrone derivatives, 0.2 mmol of the coupling product was dissolved in 6 ml of MeOH/THF (1:1) and mixed with 0.5 ml of HCl (concentrated). The solution was stirred for 12 hours at room temperature. Then, it was diluted with 20 ml of ethyl acetate. After the organic phase was separated from the aqueous phase, the organic phase was washed with water, saturated sodium bicarbonate solution and saturated sodium chloride solution, and the aqueous phase was extracted with ethyl acetate. The combined organic phases were dried on sodium sulfate, concentrated by evaporation in a rotary evaporator, and purified by flash chromatography (cyclohexane/ethyl acetate).

For production of 2-alkyl estrone derivatives, 0.2 mmol of the coupling product was dissolved in 20 ml of ethyl acetate, mixed with 100 mg of palladium on activated carbon (10%) and hydrogenated for three hours. Then, the catalyst was filtered off and concentrated by evaporation in a rotary evaporator. The residue was mixed in 20 ml of methanol, with 100 mg of sodium methanolate, and it was stirred for 12 hours. Then, it was neutralized with Amberlite IR-120 (H+), filtered and concentrated by evaporation in a rotary evaporator. The purification was carried out by flash chromatography (cyclohexane/ethyl acetate).

General Synthesis Instructions C:

2-Alkylation by ortho-Lithiation

Under an argon-cover-gas atmosphere, 5.4 ml of a 1.3 M solution of sec-butyllithium (7.0 mmol) was slowly added at −78° C. to a solution of 502 mg (1.4 mmol) of 3-methoxmethoxy-estra-1,3,5(10)-trien-17-one-17-ethylene acetal in 10 ml of THF. The reaction solution was then stirred for two hours at −78° C. and mixed with 9.8 mmol of an alkyl iodide or alkenyl iodide. The resulting mixture was stirred overnight, whereby the temperature increased to room temperature. The working-up was carried out by adding 10 ml of a saturated sodium bicarbonate solution and subsequent extraction of the aqueous phase with ethyl acetate (3×30 ml). The combined organic phases were washed with a saturated NaCl solution, dried on sodium sulfate and concentrated by evaporation in a rotary evaporator. The purification was carried out by flash chromatography (cyclohexane/ethyl acetate).

The hydrolysis of the 3-methoxy methyl ether as well as of 17-ethylene acetal was carried out according to general synthesis instructions A.

General Synthesis Instructions D:

2-Halogenation of Estrone Derivatives (P. C. Bulman Page, F. Hussain, J. L. Maggs, P. Morgan, B. K. Park, *Tetrahedron*, 1990, 46, 2059).

EXAMPLES AND PRODUCTION PROCESS

Examples 1-4 below were produced according to the above-mentioned Synthesis Instructions B.

Example 1

3-Hydroxy-2-phenylethinyl-estra-1,3,5(10)-trien-17-one 19

$^1$H-NMR (CDCl$_3$): δ=0.92 (s, 3H; 13-CH$_3$), 6.71 (s, 1H, 1-H), 7.35 (m, 4H, arom.), 7.51 (m, 2H, arom.)
$^{13}$C-NMR (CDCl$_3$): δ=220.5 (q, C=O), 154.0, 139.5, 131.9, 131.3 (2C), 128.4 (2C), 128.3, 128.2, 122.4, 114.4, 106.8 (12C, arom.) 95.4, 83.4 (2C, —C≡C—), 50.3, 47.9, 43.6, 38.1, 35.8, 31.4, 29.5, 26.3, 25.8, 21.5, 13.8

Example 2

2-Hexyl-3-hydroxy-estra-1,3,5(10)-trien-17-one 20

$^1$H-NMR (CDCl$_3$): δ=0.88 (s, 3H; 2-C$_6$H$_{13}$), 0.91 (s, 3H; 13-CH$_3$), 4.69 (br. s, 1H, OH), 6.51, 7.02 (s, 2H, 1-H, 4-H)

Example 3

3-Hydroxy-2-(2'-phenyl-ethyl)estra-1,3,5(10)-trien-17-one 21

$^1$H-NMR (CDCl$_3$): δ=0.91 (s, 3H; 13-CH$_3$), 4.74 (br. s, 1H, OH), 6.50, 7.01 (s, 2H, 1-H, 4-H), 7.19-7.30 (m, 5H, arom.)

Example 4

3-Hydroxy-2-(3'-phenyl-propyl)-estra-1,3,5(10)-trien-17-one 22

$^1$H-NMR (CDCl$_3$): δ=0.91 (s, 3H; 13-CH$_3$), 2.60 (t, 2H, $^3$J=7.8 Hz, CH$_2$CH$_2$CH$_2$-Ph), 2.69 (t, 2H, $^3$J=7.8 Hz, CH$_2$CH$_2$CH$_2$-Ph), 4.83 (br. s, 1H, OH), 6.50, 7.01 (s, 2H, 1-H, 4-H), 7.15-7.29 (m, 5H, arom.)

Examples 5-7 below were produced according to the above-mentioned Synthesis Instructions C.

Example 5

3-Hydroxy-2-methyl-estra-1,3,5(10)-trien-17-one 8

$^1$H-NMR (CDCl$_3$): δ=0.91 (s, 3H; 13-CH$_3$), 2.21 (s, 3H; 2-CH$_3$), 5.05 (br. s, 1H, OH), 6.52, 7.02 (s, 2H, 1-H, 4-H)

Example 6

3-Hydroxy-2-propyl-estra-1,3,5(10)-trien-17-one 9

$^1$H-NMR (CDCl$_3$): δ=0.91 (s, 3H; 13-CH$_3$), 0.98 (t, 3H, $^3$J=7.2 Hz, 2-Pr), 6.51, 7.02 (s, 2H, 1-H, 4-H)

Example 7

3-Hydroxy-2-(prop-2'-enyl)-estra-1,3,5(10)-trien-17-one 10

The production was carried out according to general Synthesis Instructions C. Before the addition of allyl iodide, however, the solution of the 2-metallate was first converted under argon into a solution of 8.4 mmol of copper(I) iodide in 5 ml of THF, and the resulting reaction mixture was stirred for another hour.

$^1$H-NMR (CDCl$_3$): δ=0.91 (s, 3H; 13-CH$_3$), 2.21 (s, 3H; 13-CH$_3$), 3.37 (dd, 2H, $^3$J=6.3 Hz, $^4$J=1.2 Hz, CH$_2$CH=CH$_2$), 4.99 (br. s, 1H, OH), 5.16 (m, 2H, CH$_2$CH=CH$_2$), 5.99 (m, 1H, CH$_2$CH=CH$_2$), 6.56, 7.01 (s, 2H, 1-H, 4-H)

Example 8

3-Hydroxy-2-pentanoyl-estra-1,3,5(10)-trien-17-one 2 (according to T. Nambara et al., *Chem. Pharm. Bull.* 1979, 18, 474)

$^1$H-NMR (CDCl$_3$): δ=0.93 (s, 3H; 18-CH$_3$), 0.97 (t, J=7.2 Hz, 3H; CH$_2$CH$_3$), 2.90-2.98 (m, 4H; 6-CH$_2$, CH$_2$CO), 6.71, 7.63 (2 s, 2H; 1-H, 4-H), 12.19 (s, 1H; 3-OH).

Example 9

3-Hydroxy-2-methoxymethyl-estra-1,3,5(10)-trien-17-one 7

262 mg (828 μmol) of 2-methoxymethyl-estra-1,3,5(10)-triene-3,17β-diol was dissolved in acetone, cooled to −70° C., and mixed in portions with Jones reagent (1.6 mmol). After 45 minutes, it was quenched with methanol, mixed with water and extracted with ethyl acetate. The combined organic phases were washed with a saturated sodium chloride solution, dried on sodium sulfate, and concentrated by evaporation in a rotary evaporator. Flash chromatography (n-hexane/ethyl acetate) yielded 97 mg (37%) of the desired product as colorless crystals.

$^1$H-NMR (CDCl$_3$): δ=0.91 (s, 3H; 18-CH$_3$), 2.84-2.44 (m, 2H; 6-CH$_2$), 3.42 (s, 3H; OCH$_3$), 4.57-4.65 (m, 2H; OCH$_2$), 5.44 (s, 1H; OH), 6.63, 6.92 (2 s, 2H; 1-H, 4-H), 7.24 (s, 1H; 3-OH)
$^{13}$C-NMR (CDCl$_3$): δ=220.63 (C=O).

Examples 10-12 below were produced according to the above-mentioned Synthesis Instructions D.

Example 10

2-Chloro-3-hydroxy-estra-1,3,5(10)-trien-17-one 11

$^1$H-NMR (CDCl$_3$): δ=0.91 (s, 3H; 13-CH$_3$), 5.35 (br. s, 1H, OH), 6.74, 7.20 (s, 2H, 1-H, 4-H)

Example 11

2-Chloro-3-hydroxy-18a-homoestra-1,3,5(10)-trien-17-one 1

$^1$H-NMR (CDCl$_3$): δ=0.79 (t, J=7.4 Hz, 3H; 18a-CH$_3$), 2.82-2.84 (m, 2H; 6-CH$_2$), 6.69, 7.18 (2 s, 2H; 1-H, 4-H).

Example 12

2-Cyano-3-hydroxy-estra-1,3,5(10)-trien-17-one 12

$^1$H-NMR (CDCl$_3$): δ=0.92 (s, 3H; 13-CH$_3$), 6.64, 7.35 (s, 2H, 1-H, 4-H)

Example 13

3-Hydroxy-2-methoxy-estra-1,3,5(10)-triene-6,17-dione 14

A solution of 22.2 g (222 mmol) of chromium(VI) oxide in 230 ml of dichloromethane, cooled at −35° C., was mixed [with] 22.2 g (236 mmol) of 3,5-dimethylpyrolidinone. The solution was stirred for 30 minutes at −35° C., before a solution of 5.74 g (14.79 mmol) of 2-methoxy-3-methoxmethoxy-estra-1,3,5(10)-trien-17-one-17-ethylene acetal in 10 ml of dichloromethane was added. After another two hours, the reaction mixture was mixed with 96 ml of a 5N sodium hydroxide solution, and the organic phase was separated from the aqueous phase. The aqueous phase was extracted with dichloromethane (3×50 ml). Then, the combined phases were filtered, washed with water (3×50 ml) and a saturated NaCl solution and dried on sodium sulfate. Flash chromatography yielded 1.94 g (33%) of 2-methoxy-3-methoxy-methoxy-estra-1,3,5(10)-triene-6,17-dione-17-ethylene-acetal as a colorless solid.

Of this, 100 mg (0.25 mmol) according to general Synthesis Instructions A was reacted, whereby 62 mg (80%) of the desired product was obtained as colorless crystals.

$^1$H-NMR (CDCl$_3$): δ=0.93 (s, 3H; 13-CH$_3$), 3.97 (s, 3H, 2-OCH$_3$), 5.74 (br. s, 1H, OH), 6.84, 7.60 (s, 2H, 1-H, 4-H),
$^{13}$C-NMR (CDCl$_3$): δ=219.5 (17-C), 195.8.(6-C), 151.1, 144.2, 140.2, 126.2, 112.6, 106.5 (6C, arom.), 55.9 (OCH$_3$), 50.2, 47.6, 43.1, 42.9, 39.6, 35.7, 31.2, 25.3, 21.3, 13.7

Example 14

3,7β-Dihydroxy-2-iodo-estra-1,3,5(10)-trien-17-one 15

1.86 g (6.5 mmol) of 7β-hydroxyestrone was dissolved in 25 ml of pyridine and mixed with 7 ml of acetic anhydride. The solution is stirred for 12 hours at room temperature. Then, the solvent was concentrated by evaporation in a rotary evaporator, and the oily residue was crystallized in ice water. Then, the solid was washed with water and then with n-hexane.

2.3 g of a colorless solid was obtained, which was reacted without further purification for the production of 3,7β-diacetoxy-2-iodo-estra-1,3,5(10)-trien-17-one according to P. C. Bulman Page, F. Hussain, J. L. Maggs, P. Morgan, B. K. Park, *Tetrahedron*, 1990, 46, 2059.

For the removal of both acetyl protective groups, 700 mg (1.4 mmol) of 3,7β-diacetoxy-2-iodo-estra-1,3,5(10)-trien-17-one, dissolved in 20 ml of methanol, was mixed with 200 mg of sodium methanolate, and the solution was stirred overnight. Then, it was mixed with 2.5 g of Amberlite IR-120, stirred for 30 minutes, filtered, and the solution was concentrated by evaporation in a rotary evaporator. Flash chromatography (cyclohexane/ethyl acetate) yielded 396 mg (68%) of colorless crystals.

$^1$H-NMR (DMSO-d$_6$): δ=0.81 (s, 3H; 13-CH$_3$), 2.58 (dd, 2H, $^2$J=16.0 Hz, $^3$J=7.4 Hz, 6-H), 2.82 (dd, 2H, $^2$J=16.0 Hz, $^3$J=5.9 Hz, 6-H), 3.76 (br. s, 1H, OH), 4.59 (m, 1H, 7-H), 6.60, 7.41 (s, 2H, 1-H, 4-H), 9.95 (br. s, 1H, OH)

Example 15

7β-Acetoxy-3-hydroxy-2-iodo-estra-1,3,5(10)-trien-17-one 16

700 mg (1.4 mmol) of 3,7β-diacetoxy-2-iodo-estra-1,3,5(10)-trien-17-one was dissolved in 30 ml of methanol, mixed with 1.0 g of sodium bicarbonate, and the reaction mixture was stirred overnight. Then, it was filtered, and the solution was concentrated by evaporation in a rotary evaporator. Flash chromatography (cyclohexane/ethyl acetate) yielded 402 mg (63%) of colorless crytstals.

$^1$H-NMR (DMSO-d$_6$): δ=0.82 (s, 3H; 13-CH$_3$), 2.64 (dd, 2H, $^2$J=16.6 Hz, $^3$J=6.2 Hz, 6-H), 2.99 (dd, 2H, $^2$J=16.6 Hz, $^3$J=5.8 Hz, 6-H), 5.01 (m, 1H, 7-H), 6.60, 7.45 (s, 2H, 1-H, 4-H), 10.06 (br. s, 1H, OH)

Example 16

3-Hydroxy-2-iodo-estra-1,3,5(10)-triene-7,17-dione 13

A solution of 206 mg (0.5 mmol) of 3,7β-dihydroxy-2-iodo-estra-1,3,5(10)-trien-17-one 14 in 15 ml of toluene and 4 ml of cyclohexanone was heated to 140° C. (oil bath temperature), and a solution of 400 mg of aluminum isopropylate in 10 ml of toluene was added drop by drop. In the meantime, a portion of the reaction mixture was distilled off. After complete addition of the aluminum isopropylate, it was refluxed for still another 5 hours. Then, the reaction solution was cooled and diluted with 80 ml of dichloromethane and 30 ml of potassium/sodium tartrate solution, and the resulting mixture was first stirred vigorously for 30 minutes before the organic phase was separated from the aqueous phase. The aqueous phase was finally extracted with dichloromethane (3×30 ml), and the combined organic phases were washed with a saturated NaCl solution, dried on sodium sulfate and concentrated by evaporation in a rotary evaporator. Flash chromatography (cyclohexane/ethyl acetate) yielded 129 mg (63%) of colorless crystals.

$^1$H-NMR (CDCl$_3$): δ=0.90 (s, 3H; 13-CH$_3$), 3.58 (s, 2H, 6-H), 5.62 (br. s, 1H, OH), 6.77, 7.56 (s, 2H, 1-H, 4-H)
$^{13}$C-NMR (CDCl$_3$): δ=219.5 (17-C), 208.9 (6-C), 153.7, 135.4, 133.9, 133.6, 114.2, 83.4 (6C, arom.), 50.1, 47.8, 45.3, 44.9, 40.7, 35.5, 30.5, 25.1, 23.0, 13.7

Example 17

2-Chloro-3-hydroxy-7α-methyl-estra-1,3,5(10)-trien-17-one 17

(Production analogously to Ali, H., Lier, J. E. van, *J. Chem. Soc. Perkin Trans* 1, 10, 1991, 2485)

$^1$H-NMR (CDCl$_3$): δ=0.87 (d, 3H, $^3$J=7.1 Hz, 7α-CH$_3$), 0.91 (s, 3H; 13-CH$_3$), 3.03 (dd, 1H, $^2$J=16.5 Hz, $^3$J=6.2, 6-H), 5.44 (br. s, 1H, OH), 6.73, 7.21 (s, 2H, 1H, 4-H)

Example 18

3-Hydroxy-2-methoxy-estra-1,3,5(10),6-tetraen-17-one 18

300 mg (7.94 mmol) of sodium borohydride was added to a solution of 1060 mg (2.57 mmol) of 2-methoxy-3-methoxymethoxy-estra-1,3,5(10)-triene-6,17-dione-17-ethyleneacetal in 40 ml of THF/methanol (1:1). The reaction mixture was stirred for 12 hours at room temperature and then mixed with 20 ml of water and 40 ml of ethyl acetate. The organic phase was separated from the aqueous phase. Then, the aqueous phase was with ethyl acetate (3×15 ml). The combined organic phases were washed with a saturated NaCl solution, dried on sodium sulfate and concentrated by evaporation in a rotary evaporator.

Crude product: 1040 mg of colorless solid.

700 mg of the crude product was reacted according to Synthesis Instructions A, whereby 434 mg (84%) of the desired product was obtained as colorless crystals.

$^1$H-NMR (CDCl$_3$): δ=0.92 (s, 3H; 13-CH$_3$), 3.90 (s, 3H, OCH$_3$) 5.49 (s, 1H, OH), 5.92 (dd, 1H, $^3$J=9.8 Hz, $^3$J=9.7 Hz, 7-H) 6.44 (dd, 1H, $^3$J=9.8 Hz, $^4$J=2.7 Hz, 6-H) 6.70, 6.80 (s, 2H, 1-H, 4-H)

$^{13}$C-NMR (CDCl$_3$): δ=219.9 (17-C), 145.2, 143.5, 130.6, 128.1, 127.8, 127.5, 112.5, 106.7, 56.0 (OCH$_3$), 48.8, 48.3, 42.2, 37.9, 35.7, 31.0, 23.9, 21.5, 13.6

Example 19

3-Hydroxy-2-methoxy-14α,15α-cyclopropa[a]estra-1,3,5(10),8-tetraen-17-one 5 (according to P. N. Rao et al., *Steroids* 2002, 67, 1079)

$^1$H-NMR (CDCl$_3$): δ=0.15-0.17 (m, 1H; 14α,15α-CH$_2$), 0.83-0.87 (m, 1H, 14α,15α-CH$_2$), 1.17 (s, 3H; 18-CH$_3$), 3.89 (s, 3H; OCH$_3$), 5.53 (s, 1H; OH), 6.70, 6.75 (2 s, 2H; 1-H, 4-H).

Example 20

2-Chloro-16-fluoro-3-hydroxy-estra-1,3,5(10)-trien-17-one

A solution of 58 mg (188 μmol) of 2-chloro-3-hydroxy-estra-1,3,5(10)-trien-17-one in 10 ml of methanol was mixed with 190 mg of 1-fluoro-4-hydroxy-1,4-diazonia-bicyclo[2,2,2]-octane-bis(tetrafluoroborate) on aluminum oxide, and it was refluxed for five hours. Then, it was cooled to room temperature, mixed with 1N hydrochloric acid, and extracted with dichloromethane. The organic phases were dried on sodium sulfate and concentrated by evaporation in a rotary evaporator. Purification by means of HPLC (Chiracel OJ-H, n-heptane/2-propanol) yielded about 10 mg each of the two stereoisomers.

2-Chloro-16α-fluoro-3-hydroxy-estra-1,3,5(10)-trien-17-one 3

$^1$H-NMR (CDCl$_3$): δ=0.96 (s, 3H; 18-CH$_3$), 5.32 (dd, J$_{HF}$=50.8, J$_{HH}$=7.2 Hz, 1H; 16β-H), 5.37 (s, 1H; OH), 6.75, 7.19 (2 s, 2H; 1-H, 4-H)—$^{19}$F-NMR (CDCl$_3$): δ=192.228--192.56 (m).

2-Chloro-16β-fluoro-3-hydroxy-estra-1,3,5(10)-trien-17-one 4

$^1$H-NMR (CDCl$_3$): δ=1.04 (s, 3H; 18-CH$_3$), 2.84-2.88 (m, 2H; 6-CH$_2$), 4.76 (ddd, J$_{HF}$=50.0, J$_{HH}$=8.2, 8.6 Hz, 1H; 16α-H), 5.36 (s, 1H; OH), 6.75, 7.19 (2 s, 2H; 1-H, 4-H)—$^{19}$F-NMR (CDCl$_3$): δ=–192.20 (dd, J=50.1, 21.5 Hz).

Example 21

3-Hydroxy-2-methoxy-estra-1,3,5(10)-triene-17-thione 6

A solution of 1.09 g (3.63 mmol) of 3-hydroxy-2-methoxy-estra-1,3,5(10)-trien-17-one in 60 ml of toluene (abs.) was mixed with 3.7 g of Lawesson's reagent, and it was refluxed for four hours. After water was added, it was extracted with dichloromethane (3×), and the combined organic phases were washed with water, dried on sodium sulfate, and concentrated by evaporation in a rotary evaporator. Flash chromatography (n-hexane/ethyl acetate) yielded 412 mg (36%) of the desired product as yellow crystals.

$^1$H-NMR (CDCl$_3$): δ=0.95 (s, 3H; 18-CH$_3$), 2.70 (ddd, J=8.6, 8.6, 21.9 Hz, 1H, 16-H), 2.76-2.90 (m, 2H; 6-CH$_2$), 3.02 (ddd, J=1.2, 8.6, 21.9 Hz, 1H; 16H'), 3.87 (s, 3H; OCH$_3$), 5.44 (s, 1H; OH), 6.66, 6.79 (2 s, 2H; 1-H, 4-H), 12.19 (s, 1H; 3-OH).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosures of all applications, patents and publications, cited herein and of corresponding German application No. 102004032674.6, filed Jul. 2, 2004 and U.S. Provisional Application Ser. No. 60/584,482, filed Jul. 2, 2004, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A 2-substituted estra-1,3,5(10)-trien-17-one compound of formula I

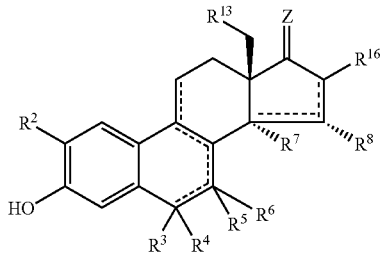

in which
R$^2$ means phenylethyl, phenylpropyl or phenylethinyl,
R$^{13}$ means a hydrogen atom or a methyl group,
R$^{16}$ means a hydrogen atom or a fluorine atom,
Z means an oxygen atom or a sulfur atom,
R$^3$ and R$^5$ mean, in each case independently of one another, an α- or β-position hydrogen atom,
R$^4$ and R$^6$ mean, in each case independently of one another, an α- or β-position hydrogen atom, a C$_1$-C$_5$-alkyl group, a C$_1$-C$_5$-alkyloxy group, a C$_1$-C$_5$-acyl group, a hydroxy group, an aralkyl or heteroaralkyl radical, or an alkylaryl or alkylheteroaryl radical,
R$_3$ and R$_4$ together can also be an oxygen atom,
R$_5$ and R$_6$ together can also be an oxygen atom,
R$^7$ and R$^8$ in each case mean a hydrogen atom or together a CH$_2$ group,
wherein the aryl or heteroaryl groups are unsubstituted or substituted by methyl, ethyl, trifluoromethyl, pentafluoroethyl, trifluoromethylthio, methoxy, ethoxy, nitro, cyano, halogen, hydroxy, amino, mono(C$_{1-8}$-alkyl)amino, di(C$_{1-8}$-alkyl)amino wherein the alkyl groups are identical or different, or di(aralkyl)amino wherein the aralkyl groups are identical or different, and
wherein the dotted lines in the B-, C- and D-ring of the steroid skeleton additionally can be up to two double bonds,
or a pharmaceutically acceptable salt thereof.

2. A compound according to claim 1, wherein R$^2$ is phenylethyl, or phenylpropyl.

3. A compound according to claim 1, wherein R$^{13}$ is a hydrogen atom.

4. A compound according to claim 1, wherein R$^2$ is a phenylethinyl group.

5. A pharmaceutical composition comprising a compound according to claim 1 and a pharmaceutically acceptable carrier.

6. A pharmaceutical composition according to claim 5, further comprising at least one other active ingredient.

7. A pharmaceutical composition according to claim 6, wherein the at least one other active ingredient is an antiandrogen, antigestagen, aromatase inhibitor or an antiestrogen.

8. A 2-substiftited estra-1,3,5(10)-trien-17-one compound of formula I

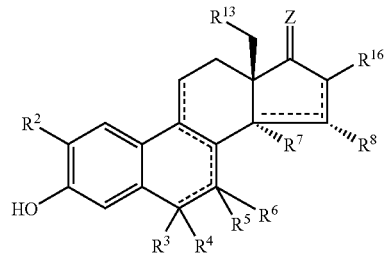

in which
R$^2$ means a C$_1$-C$_5$-alkyloxy group, an aralkyl or heteroaralkyl radical, an alkylaryl or alkyiheteroaryl radical, a radical —O—C$_n$F$_m$H$_o$, a group CH$_2$XY, a phenylethinyl group, a chlorine, iodine, or bromine atom or a nitrile group,
n is 1, 2, 3, 4, 5 or 6,
m is ≧1,
m+o is=2n+1,
X is an oxygen atom,
Y is an alkyl radical with 1 to 4 carbon atoms,
R$^{13}$ means a hydrogen atom or a methyl group,
R$^{16}$ means a fluorine atom,
Z means an oxygen atom or a sulfur atom,
R$^3$ and R$^5$ mean, in each case independently of one another, an α- or β-position hydrogen atom,
R$^4$ and R$^6$ mean, in each case independently of one another, an α- or β-position hydrogen atom, a C$_1$-C$_5$-alkyl group, a C$_1$-C$_5$-alkyloxy group, a C$_1$-C$_5$-acyl group, a hydroxy group, an aralkyl or heteroaralkyl radical, or an alkylaryl or alkylheteroaryl radical,
R$_3$ and R$_4$ together can also be an oxygen atom,
R$_5$ and R$_6$ together can also be an oxygen atom,
R$^7$ and R$^8$ in each case mean a hydrogen atom or together a CH$_2$ group,
wherein the aryl or heteroaryl groups are unsubstituted or substituted by methyl, ethyl, trifluoromethyl, pentafluoroethyl, trifluoromethylthio, methoxy, ethoxy, nitro, cyano, halogen, hydroxy, amino, mono(C$_{1-8}$-alkyl)amino, di(C$_{1-8}$-alkyl)amino wherein the alkyl groups are identical or different, or di(aralkyl)amino wherein the aralkyl groups are identical or different, and
wherein the dotted lines in the B-, C- and D-ring of the steroid skeleton additionally can be up to two double bonds,
or a pharmaceutically acceptable salt thereof.

9. A compound according to claim 8, wherein R$^2$ is a C$_4$-C$_5$-alkyloxy group, an arallcyl or an alkylaryl radical, a radical —O—C$_n$F$_m$H$_o$, a group CH$_2$XY, or a phenylethinyl group.

10. A compound according to claim 8, wherein R$^2$ is a chlorine atom.

11. A compound according to claim 8, wherein R$^2$ is a C$_1$-C$_5$-alkyloxy group, an aralkyl or heteroaralkyl radical, an alkylaryl or alkyiheteroaryl radical, a radical —O—C$_n$F$_m$H$_o$, a group CH$_2$XY, a phenylethinyl group, or a nitrile group.

12. A compound according to claim 10, wherein R$^{13}$ is a hydrogen atom.

13. A compound according to claim 8, wherein R$^2$ is an aralkyl or heteroaralkyl radical, an alkylaryl or alkyiheteroaryl radical, a radical —O—C$_n$F$_m$H$_o$, a group CH$_2$XY, a phenylethinyl group, a chlorine, iodine, or bromine atom or a nitrile group.

14. A 2-substituted estra-1,3,5 (10)-trien-17-one compound of formula I

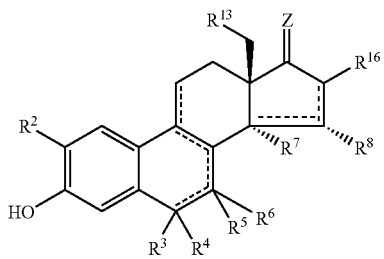

in which

R$^2$ means a C$_1$-C$_5$-alkyloxy group, an aralkyl or heteroaralkyl radical, an alkylaryl or alkyiheteroaryl radical, a radical —O—C$_n$F$_m$H$_o$, a group CH$_2$XY, a phenylethinyl group, a halogen atom, or a nitrile group, n is 1, 2, 3, 4, 5 or 6,
m is≧1,
m+o is=2n=1,
X is an oxygen atom,
Y is an alkyl radical with 1 to 4 carbon atoms,
R$^{13}$ means a hydrogen atom or a methyl group,
R$^{16}$ means a fluorine atom,
Z means an oxygen atom or a sulfur atom,
R$^3$ and R$^5$ mean, in each case independently of one another, an α- or β-position hydrogen atom,
R$^4$ and R$^6$ mean, in each case independently of one another, an α- or β-position hydrogen atom, a C$_1$-C$_5$-alkyl group, a C$_1$-C$_5$-alkyloxy group, a C$_1$-C$_5$-acyl group, a hydroxy group, an aralkyl or heteroaralkyl radical, or an alkylaryl or alkylheteroaryl radical,
R$_3$ and R$_4$ together can also be an oxygen atom,
R$_5$ and R$_6$ together can also be an oxygen atom,
R$^7$ and R$^8$ in each case mean a hydrogen atom or together a CH$_2$ group,
wherein the aryl or heteroaryl groups are unsubstituted or substituted by methyl, ethyl, trifluoromethyl, pentafluoroethyl, trifluoromethylthio, methoxy, ethoxy, nitro, cyano, halogen, hydroxy, amino, mono(C$_{1-8}$-alkyl)amino, di(C$_{1-8}$-alkyl)amino wherein the alkyl groups are identical or different, or di(aralkyl)amino wherein the aralkyl groups are identical or different, and
wherein the dotted lines in the B-, C- and D-ring of the steroid skeleton additionally can be up to two double bonds,
or a pharmaceutically acceptable salt thereof.

15. A compound according to claim 14, wherein R$^2$ is a C$_4$-C$_5$-alkyloxy group, an aralkyl or an alkylaryl radical, a radical —O—C$_n$F$_m$H$_o$, a group CH$_2$XY, or a phenylethinyl group.

16. A 2-substituted estra-1,3,5(10)-trien-17-one compound of formula I

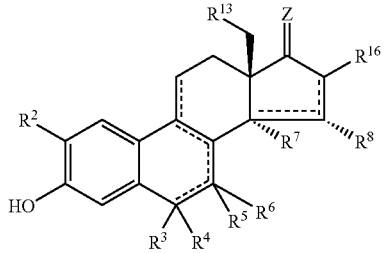

in which

R$^2$ means a C$_1$-C$_5$-alkyloxy group, an aralkyl or heteroaralkyl radical, an alkylaryl or alkyiheteroaryl radical, a radical —O—C$_n$F$_m$H$_o$, a group CH$_2$XY, a phenylethinyl group, a halogen atom, or a nitrile group, n is 1, 2, 3, 4, 5 or 6,
m is≧1,
m+o is=2n=1,
X is an oxygen atom,
Y is an alkyl radical with 1 to 4 carbon atoms,
R$^{13}$ means a hydrogen atom or a methyl group,
R$^{16}$ means a fluorine atom,
Z means an oxygen atom or a sulfur atom,
R$^3$ and R$^5$ mean, in each case independently of one another, an α- or β-position hydrogen atom,
R$^4$ and R$^6$ mean, in each case independently of one another, an α- or β-position hydrogen atom, a C$_1$-C$_5$-alkyl group, a C$_1$-C$_5$-alkyloxy group, a C$_1$-C$_5$-acyl group, a hydroxy group, an aralkyl or heteroaralkyl radical, or an alkylaryl or alkylheteroaryl radical,
R$^7$ and R$^8$ in each case mean a hydrogen atom or together a CH$_2$ group,
wherein the aryl or heteroaryl groups are unsubstituted or substituted by methyl, ethyl, trifluoromethyl, pentafluoroethyl, trifluoromethylthio, methoxy, ethoxy, nitro, cyano, halogen, hydroxy, amino, mono(C$_{1-8}$-alkyl)amino, di(C$_{1-8}$-alkyl)amino wherein the alkyl groups are identical or different, or di(aralkyl)amino wherein the aralkyl groups are identical or different, and
wherein the dotted lines in the B-, C- and D-ring of the steroid skeleton additionally can be up to two double bonds,
or a pharmaceutically acceptable salt thereof.

17. A compound according to claim 16, wherein R$^2$ is a C$_4$-C$_5$-alkyloxy group, an aralkyl or an alkylaryl radical, a radical —O—C$_n$F$_m$H$_o$, a group CH$_2$XY, or a phenylethinyl group.

18. A compound according to claim 16, wherein R$^2$ is an aralkyl or an alkylaryl radical, a radical —O—C$_n$F$_m$H$_o$, a group CH$_2$XY, or a phenylethinyl group.

19. A method for the therapy of hormone-dependent tumor disease of a male or female reproductive gland, male or female sex organ, or a mammary gland comprising administering to a patient in need thereof an effective amount of a pharmaceutical composition according to claim 5.

20. A method for the therapy of breast cancer comprising administering to a patient in need thereof an effective amount of a pharmaceutical composition according to claim 5.

21. A method for the therapy of prostate cancer comprising administering to a patient in need thereof an effective amount of a pharmaceutical composition according to claim 5.

22. A method for treating endometriosis comprising administering to a patient in need thereof an effective amount of a pharmaceutical composition according to claim 5.

23. A method of treating breast cancer, prostate cancer, or endometriosis comprising administering to a patient in need thereof an effective amount of a pharmaceutical composition comprising a compound according to claim 1 and a pharmaceutically acceptable carrier.

24. A method of treating breast cancer, prostate cancer, or endometriosis comprising administering to a patient in need thereof an effective amount of a pharmaceutical composition comprising a compound according to claim 8 and a pharmaceutically acceptable carrier.

25. A method of treating breast cancer, prostate cancer, or endometriosis comprising administering to a patient in need thereof an effective amount of a pharmaceutical composition comprising a compound according to claim 14 and a pharmaceutically acceptable carrier.

26. A method of treating breast cancer, prostate cancer, or endometriosis comprising administering to a patient in need thereof an effective amount of a pharmaceutical composition comprising a compound according to claim 16 and a pharmaceutically acceptable carrier.

* * * * *

UNITED STATES PATENT AND TRADEMARK OFFICE
CERTIFICATE OF CORRECTION

PATENT NO. : 7,419,972 B2  Page 1 of 1
APPLICATION NO. : 11/154947
DATED : September 2, 2008
INVENTOR(S) : Alexander Hillisch It is certified that error appears in the above-identified patent and that said Letters Patent is hereby corrected as shown below:

Column 19, line 40, reads "trifiuoromethylthio," should read -- trifluoromethylthio, --
Column 19, line 66, reads "2-substiftited" should read -- 2-substituted --
Column 20, line 17, reads "alkyiheteroaryl" should read -- alkylheteroaryl --
Column 20, line 22, reads "m is≥1," should read -- m is ≥ 1, --
Column 20, line 23, reads "m+o is=2n=1," should read -- m + o is = 2n + 1, --
Column 20, line 52, reads "arallcyl" should read -- aralkyl --
Column 20, line 59, reads "alkyiheteroaryl" should read -- alkylheteroaryl --
Column 20, line 64-65, reads "alkyiheteroaryl" should read -- alkylheteroaryl --
Column 21, line 28, reads "alkyiheteroaryl" should read -- alkylheteroaryl --
Column 21, line 29, reads "—O—$C^{n}F^{m}H^{o}$," should read -- —O—$C_nF_mH_o$, --
Column 21, line 33, reads "m is≥1," should read -- m is ≥ 1, --
Column 21, line 34, reads "m+o is=2n=1," should read -- m + o is = 2n + 1, --
Column 21, line 38, reads "a fluorine" should read -- a hydrogen atom or a fluorine --
Column 21, line 49, reads "in each case mean a hydrogen atom or together" should read -- mean together --
Column 22, line 23, reads "$C_1$-$C_5$-alkoxy group," should read -- $C_4$-$C_5$-alkoxy group, --
Column 22, line 24, reads "alkyiheteroaryl" should read -- alkylheteroaryl --
Column 22, line 28, reads "m is≥1," should read -- m is ≥ 1, --
Column 22, line 29, reads "m+o is=2n=1," should read -- m + o is = 2n + 1, --
Column 22, line 33, reads "a fluorine" should read -- a hydrogen atom or a fluorine --
Column 22, following line 43 ("a CH$_2$ group,") and before line 44 ("wherein the aryl. . ."), insert a new line reading -- wherein at least one of $R^3$ and $R^4$ or $R^5$ and $R^6$ together mean an oxygen atom, --

Signed and Sealed this

Seventeenth Day of March, 2009

JOHN DOLL
*Acting Director of the United States Patent and Trademark Office*